United States Patent
Georgeson

(10) Patent No.: US 9,726,644 B2
(45) Date of Patent: Aug. 8, 2017

(54) NONDESTRUCTIVE INSPECTION USING ACOUSTO-OPTICS

(71) Applicant: The Boeing Company, Chicago, IL (US)

(72) Inventor: Gary Ernest Georgeson, Tacoma, WA (US)

(73) Assignee: THE BOEING COMPANY, Chicago, IL (US)

(*) Notice: Subject to any disclaimer, the term of this patent is extended or adjusted under 35 U.S.C. 154(b) by 388 days.

(21) Appl. No.: 14/328,905

(22) Filed: Jul. 11, 2014

(65) Prior Publication Data
US 2016/0011152 A1 Jan. 14, 2016

(51) Int. Cl.
*G01N 29/04* (2006.01)
*G01N 29/06* (2006.01)
*G01N 29/11* (2006.01)
*G01N 29/24* (2006.01)

(52) U.S. Cl.
CPC ....... *G01N 29/2418* (2013.01); *G01N 29/043* (2013.01); *G01N 29/048* (2013.01); *G01N 29/0654* (2013.01); *G01N 29/11* (2013.01); *G01N 2291/0231* (2013.01); *G01N 2291/2694* (2013.01)

(58) Field of Classification Search
CPC ............... G01N 29/043; G01N 29/048; G01N 29/0654; G01N 29/4518; G01N 29/11; G01N 2291/2694; G01N 2291/0231
USPC .......................................................... 73/655
See application file for complete search history.

(56) References Cited

U.S. PATENT DOCUMENTS

| | | | | |
|---|---|---|---|---|
| 5,909,279 A | * | 6/1999 | Pepper ................... | G01H 9/006 356/479 |
| 7,694,567 B2 | * | 4/2010 | Haupt ..................... | F41H 11/12 73/594 |
| 8,255,170 B2 | | 8/2012 | Kollgaard et al. | |
| 2003/0014199 A1 | * | 1/2003 | Toomey ................. | G01H 9/002 702/56 |
| 2004/0092808 A1 | | 5/2004 | Ogawa | |
| 2012/0157837 A1 | | 6/2012 | Nagata et al. | |
| 2013/0160552 A1 | * | 6/2013 | Nakata ............... | G01N 29/2418 73/628 |

(Continued)

FOREIGN PATENT DOCUMENTS

EP          2703806 A1     3/2014

OTHER PUBLICATIONS

Adams, "Nonlinear Dynamics . . . to see what is unseen in lightweight blades," LASIR Laboratory for Systems Integrity & Reliability, Nov. 5, 2013, 37 pages.

(Continued)

*Primary Examiner* — J M Saint Surin
(74) *Attorney, Agent, or Firm* — Yee & Associates, P.C.

(57) ABSTRACT

A method and apparatus for inspecting an object. The apparatus comprises a vibration generator and an acousto-optical sensor. The vibration generator is positioned relative to a surface of an object. The vibration generator excites the object at a location on the object such that the portion of the object vibrates. The acousto-optical sensor is coupled to the surface of the portion of the object. The acousto-optical sensor detects a vibratory response generated by the portion of the object in response to excitation of the portion of the object and generates an image of the portion of the object based on the vibratory response.

19 Claims, 10 Drawing Sheets

(56) References Cited

U.S. PATENT DOCUMENTS

2013/0174639 A1* 7/2013 Earthman ............... A61B 9/00
73/12.01
2014/0060188 A1* 3/2014 Singh .................... G01N 29/12
73/579
2014/0121490 A1 5/2014 Hashimoto et al.

OTHER PUBLICATIONS

Solodov "Resonance of defects: an advance toward efficient non-linear ultrasonic NDE and ultrasonic thermography," Dresden Airport Seminar, Nov. 6, 2013, 35 pages.
Extended European Search Report, dated Nov. 11, 2015, regarding Application No. EP15176341.4, 7 pages.
Sinha D. N. "Acoustic resonance spectroscopy (ARS)," IEEE Potentials, IEEE vol. 11 No. 2, Apr. 1, 1992, 4 pages.

* cited by examiner

NONDESTRUCTIVE INSPECTION USING ACOUSTO-OPTICS

BACKGROUND INFORMATION

1. Field

The present disclosure relates generally to inspection systems and, in particular, to nondestructive inspection systems. Still more particularly, the present disclosure relates to a method and apparatus for nondestructively inspecting an object using acousto-optics to determine whether a feature of interest is present in the object.

2. Background

Nondestructive inspection (NDI) systems are oftentimes used to inspect different types of objects, including composite structures. Nondestructive inspection systems allow an object to be inspected without affecting the object in an undesired manner. In some cases, a nondestructive system may also be referred to as a nondestructive testing (NDT) system or a nondestructive evaluation (NDE) system.

A variety of nondestructive inspection methods are currently available for use with composite structures. However, some of these currently available methods are slower and more expensive than desired. Further, some of these currently available methods may require an expert in nondestructive inspection to perform the nondestructive inspection.

For example, some currently available ultrasonic nondestructive inspection methods, including ultrasonic pulse echo methods, may be more expensive than desired, may be slow to run, may require an expert to perform the inspection, or some combination thereof. A low-frequency bond testing method may be used, but this method may also be slower than desired in some cases. Further, an expert in nondestructive inspection may also be needed to perform low-frequency bond testing.

While faster methods such as laser shearography and infrared thermography able to provide results in substantially real-time are known, these may be prohibitively expensive. Providing results in substantially "real-time" means providing results without significant delay between the performance of the inspection of an object and the generation of the results. These results may take the form of, for example, images, that provide visual indications of whether undesired features of interest are present in an object. The results may then be analyzed or interpreted by, for example, a human operator at the same time at which the results are generated or at some later time. Further, infrared thermography may be unable to detect certain types of features, such as "kissing" bonds. A "kissing" bond may be a bond between two parts that have been positioned and coupled relative to each other with substantially no gap or space present between these parts. This coupling may have been performed using, for example, an adhesive. This type of bond may have reduced strength and, in some cases, substantially zero strength.

Thus, these currently available nondestructive inspection methods may be unable to provide the type of fast, simple, and inexpensive inspection that may be useful in certain situations. Therefore, it would be desirable to have a method and apparatus for performing nondestructive inspection that take into account at least some of the issues discussed above, as well as other possible issues.

SUMMARY

In one illustrative embodiment, an apparatus comprises a vibration generator and an acousto-optical sensor. The vibration generator is positioned relative to a surface of an object. The vibration generator excites the object at a location on the object such that at least a portion of the object vibrates. The acousto-optical sensor is coupled to the surface of the portion of the object. The acousto-optical sensor detects a vibratory response generated by the portion of the object in response to excitation of the portion of the object and generates an image of the portion of the object based on the vibratory response.

In another illustrative embodiment, a nondestructive inspection system comprises a vibration generator, an acousto-coupling sensor, and a coupling element. The vibration generator is positioned relative to a surface of an object. The vibration generator excites the object at an ultrasonic frequency at a location on the object such that at least a portion of the object vibrates. The acousto-optical sensor is coupled to the surface of the portion of the object. The acousto-optical sensor detects a vibratory response generated by the portion of the object in response to excitation of the portion of the object and generates an image of the portion of the object based on the vibratory response. The vibratory response includes a feature response that is produced when a feature is present within the portion of the object such that the image of the portion of the object included a visual representation of the feature. The coupling element couples the acousto-optical sensor to the surface of the portion of the object to facilitate transmission of acoustic energy from the portion of the object to the acousto-optical sensor.

In yet another illustrative embodiment, a method for inspecting an object is provided. The object is excited at a location on the object using a vibration generator positioned relative to a surface of the object such that at least a portion of the object vibrates. A vibratory response generated by the portion of the object is detected in response to excitation of the object using an acousto-optical sensor coupled to the surface of the portion of the object. An image of the portion of the object is generated, by the acousto-optical sensor, based on the vibratory response.

The features and functions can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the illustrative embodiments are set forth in the appended claims. The illustrative embodiments, however, as well as a preferred mode of use, further objectives and features thereof, will best be understood by reference to the following detailed description of an illustrative embodiment of the present disclosure when read in conjunction with the accompanying drawings, wherein:

DETAILED DESCRIPTION

The illustrative embodiments recognize and take into account different considerations. For example, the illustrative embodiments recognize and take into account that it may be desirable to have a nondestructive inspection system that does not require an expert to perform the inspection. A nondestructive inspection system that does not require an expert in nondestructive inspection to be present on-site for the inspection may reduce some of the costs associated with the inspection.

For example, it may be desirable for a non-expert to perform an inspection of an object, while an expert located remotely views and analyzes the results of the inspection in substantially real-time. In other cases, it may be desirable to generate the results of the inspection in substantially real-time but have the expert view and analyze the results at a later time.

The illustrative embodiments also recognize and take into account that it may be desirable to have a nondestructive inspection system that can produce high-resolution images of features of interest in objects in substantially real-time, while still being lightweight and portable. The illustrative embodiments recognize and take into account that acousto-optical sensors may be lightweight, portable, and capable of producing high-resolution images. Thus, the illustrative embodiments provide a method, apparatus, and system for performing nondestructive inspection using acousto-optics.

In one illustrative example, an object is mechanically excited at a location on the object using a vibration generator positioned relative to a surface of the object such that at least a portion of the object vibrates. An acousto-optical sensor coupled to the surface of the portion of the object is used to detect a vibratory response generated by the portion of the object. The acousto-optical sensor generates an image of the portion of the object based on the vibratory response.

When a feature of interest is present within the portion of the object, the vibratory response may include a feature response corresponding to the feature of interest. The feature response may be a portion of the vibratory response that behaves differently from a rest of the vibratory response generated by the portion of the object. For example, the feature response may be more nonlinear in response to the excitation of the object, whereas the rest of the vibratory response may be more linear. Consequently, the image generated may include a visual representation of the feature of interest that is distinguishable from the visual representation of a rest of the portion of the object in the image.

Figure 1:
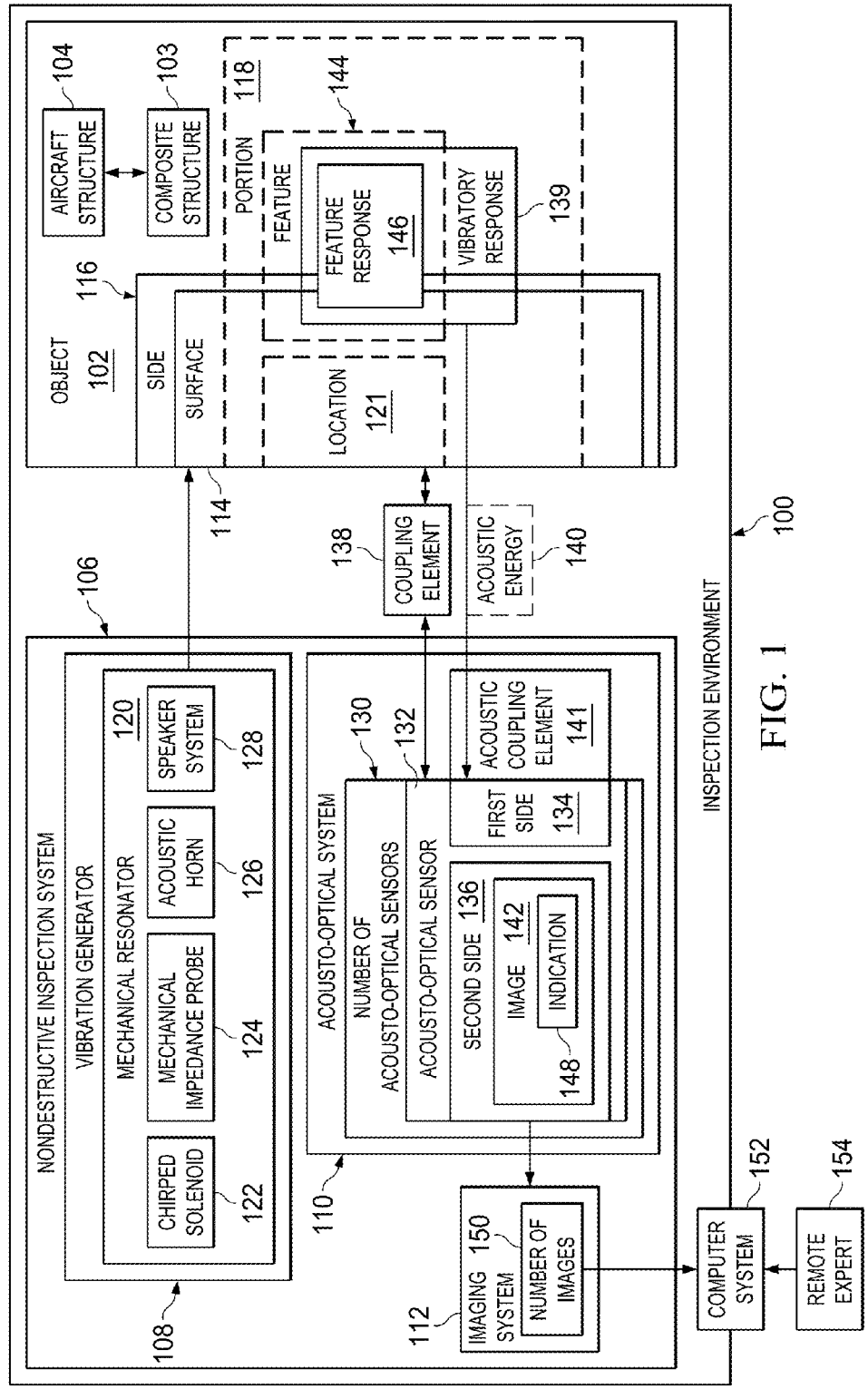
FIG. 1 is an illustration of an inspection environment in the form of a block diagram in accordance with an illustrative embodiment.

Referring now to the figures and, in particular, with reference to FIG. 1, an illustration of an inspection environment is depicted in the form of a block diagram in accordance with an illustrative embodiment. In this illustrative example, inspection environment 100 is any environment in which an object, such as object 102, may be inspected.

Object 102 may take a number of different forms. In one illustrative example, object 102 may take the form of composite structure 103. In other words, composite structure 103 may be comprised of composite material. Composite structure 103 may take a number of different structural forms. For example, without limitation, composite structure 103 may take the form of a laminated, sandwiched, or honeycomb structure, or some other type of composite structure. In other illustrative examples, object 102 may take the form of a non-composite structure or a partially composite structure. For example, object 102 may be comprised of any number of metals, metal alloys, plastic materials, composite materials, or combination thereof.

In one illustrative example, object 102 may take the form of aircraft structure 104. Aircraft structure 104 may be an example of one implementation for composite structure 103 in some cases. Aircraft structure 104 may be selected from a group consisting of a fuselage, a wing, a spar, a rib, a skin panel, an aileron, a flap, a stabilizer, or some other type of aircraft part or assembly of aircraft parts. These aircraft parts may be composite parts in some illustrative examples. In other illustrative examples, object 102 may take the form of a door, a wall, or some other type of structure.

As depicted, nondestructive inspection system 106 may be used to inspect object 102. In particular, nondestructive inspection system 106 may be used to inspect at least portion 118 of object 102 to determine whether one or more features of interest are present within portion 118 of object 102. As used herein, a "portion" of an item, such as portion 118 of object 102, may be an area of the object 102 such as a section, a piece, or a part of the entire object 102. In other illustrative examples, portion 118 may be the entirety of object 102. In some cases, portion 118 of object 102 may include an area of object 102 at which a bond is located. The bond may take a number of different forms, one of which may be a "kissing" bond.

A feature of interest may be, for example, a particular layer in object 102, a part that has been bonded to object 102, a membrane, or some other type of feature. In some illustrative examples, the feature of interest may be an undesired feature. As used herein, an "undesired feature" may be any inconsistency in object 102 that is undesired. For example, an undesired feature may be a disbond, a crack, a micro-crack, a delamination, a wrinkle, foreign object debris (FOD), a void, an undesired porosity, or some other type of feature that is not desirable for object 102. A disbond may be a bond that has been weakened such that a strength of the bond is below some selected threshold. In some cases, the bond may have been weakened to the extent that the bond has substantially zero strength.

As depicted, nondestructive inspection system 106 includes vibration generator 108 and acousto-optical system 110. In some illustrative examples, nondestructive inspection system 106 may also include imaging system 112.

Vibration generator 108 may be positioned relative to surface 114 of object 102 at side 116 of object 102. In one illustrative example, vibration generator 108 may be positioned such that vibration generator 108 is in physical contact with object 102. In other illustrative examples, vibration generator 108 may be positioned relative to object 102 but not in physical contact with object 102.

Vibration generator 108 is configured to excite object 102 such that object 102 vibrates. In these illustrative examples, exciting object 102 may mean exciting some portion of object 102 or all of object 102. For example, vibration generator 108 may be configured to excite object 102 at location 121 on object 102 such that at least portion 118 of object 102 is vibrated. Thus, exciting object 102 at location 121 may excite some or all of object 102. Location 121 may be within portion 118 of object 102, around portion 118 of object 102, or within some selected distance from portion 118 of object 102.

Vibration generator 108 excites object 102 at ultrasonic frequencies. These ultrasonic frequencies may be between about 1 kilohertz and about 500 kilohertz. In these illustrative examples, vibration generator 108 mechanically excites object 102. Mechanically exciting object 102 may mean physically exciting object 102. For example, vibration generator 108 may be used to physically contact object 102 repeatedly at an ultrasonic frequency to excite at least portion 118 of object 102.

In other illustrative examples, vibration generator 108 may direct ultrasonic waves towards object 102 that cause surface displacement at surface 114 of at least portion 118 of object 102 when the ultrasonic waves impinge upon, or encounter, surface 114. In this manner, the ultrasonic waves impinging upon object 102 excite object 102 such that at least portion 118 of object 102 vibrates.

Vibration generator 108 may take a number of different forms. For example, vibration generator 108 may take the form of mechanical resonator 120. Mechanical resonator 120 may be selected from one of chirped solenoid 122, mechanical impedance probe 124, acoustic horn 126, speaker system 128, or some other type of mechanical resonator.

Mechanical resonator 120 may cause portion 118 of object 102 to vibrate and any features of interest that may be present within portion 118 of object 102 to vibrate. For example, a feature of interest, such as feature 144, may be present within portion 118 of object 102. When a frequency at which portion 118 of object 102 is excited is substantially equal to a natural frequency of feature 144 that is present within portion 118 of object 102 within selected tolerances, feature 144 may resonate. A frequency within selected tolerances of the natural frequency of feature 144 may be a frequency within some number of hertz or kilohertz from the natural frequency. This number may be, for example, but is not limited to, 1 hertz, 5 hertz, 10 hertz, 1 kilohertz, 2 kilohertz, 5 kilohertz, or some other number of hertz or kilohertz.

When the feature resonates, the vibration of feature 144 may be amplified relative to the vibration of a rest of portion 118 of object 102. Feature 144 may resonate when excited at or within a certain range of the natural frequency of feature 144. The natural frequency of feature 144 is the frequency at which feature 144 tends to oscillate in the absence of any driving or damping forces.

Acousto-optical system 110 may be implemented using acoustography, which is an ultrasound imaging technique that uses a super high-resolution ultrasound detector to produce ultrasound images. Acousto-optical system 110 may include number of acousto-optical sensors 130. As used herein, a "number of" items may include one or more items. In this manner, number of acousto-optical sensors 130 may include one or more acousto-optical sensors. Acousto-optical sensor 132 is an example of one of number of acousto-optical sensors 130. Acousto-optical sensor 132 may be implemented using one of the acousto-optical (AO) sensors provided by Santec Systems, Incorporated, headquartered in Wheeling, Ill.

As depicted, acousto-optical sensor 132 has first side 134 and second side 136. Acousto-optical sensor 132 is positioned relative to portion 118 of object 102 such that first side 134 faces surface 114 of portion 118 of object 102. In this manner, acousto-optical sensor 132 may be coupled to a same side 116 of object 102 as vibration generator 108.

First side 134 of acousto-optical sensor 132 may be coupled to surface 114 of portion 118 of object 102 using coupling element 138. Coupling element 138 may take the form of a physical element, a force, a pressure, or some combination thereof used to retain first side 134 of acousto-optical sensor 132 in a fixed position relative to portion 118 of object 102. In some illustrative examples, coupling element 138 may retain acousto-optical sensor 132 in physical contact with surface 114.

Depending on the implementation, coupling element 138 may comprise at least one element selected from a group consisting of a vacuum seal, an adhesive, mechanical pressure applied to acousto-optical sensor 132, an adhesion system, or some other type of element configured for holding acousto-optical sensor 132 in place relative to portion 118 of object 102. The mechanical pressure may be applied by, for example, without limitation, a human operator holding acousto-optical sensor 132 against surface 114 of portion 118 of object 102.

Acousto-optical sensor 132 detects vibratory response 139 generated by portion 118 of object 102 in response to the excitation of object 102 by vibration generator 108. Vibratory response 139 may be detected as acoustic energy 140. In one illustrative example, acoustic energy 140 produced by object 102 in response to the excitation of object 102 may form a resonance pattern.

In this illustrative example, acousto-optical sensor 132 receives acoustic energy 140 generated by vibration of object 102 at first side 134. As depicted, acoustic coupling element 141 may be associated with first side 134 of acousto-optical sensor 132 to facilitate the transmission of acoustic energy 140 from object 102 to acousto-optical sensor 132. As used herein, when one component is "associated" with another component, the association is a physical association in the depicted examples.

For example, a first component, such as acoustic coupling element 141, may be considered to be associated with a second component, such as acousto-optical sensor 132, by being at least one of secured to the second component, bonded to the second component, mounted to the second component, welded to the second component, fastened to the second component, or connected to the second component in some other suitable manner. The first component also may be connected to the second component using a third component. Further, the first component may be considered to be associated with the second component by being formed as part of the second component, an extension of the second component, or both.

As used herein, the phrase "at least one of," when used with a list of items, means different combinations of one or more of the listed items may be used and only one of the items in the list may be needed. The item may be a particular object, thing, action, process, or category. In other words, "at least one of" means any combination of items or number of items may be used from the list, but not all of the items in the list may be required.

For example, "at least one of item A, item B, and item C" or "at least one of item A, item B, or item C" may mean item A; item A and item B; item B; item A, item B, and item C; or item B and item C. In some cases, "at least one of item A, item B, and item C" may mean, for example, without limitation, two of item A, one of item B, and ten of item C; four of item B and seven of item C; or some other suitable combination.

Acoustic coupling element 141 may include a substance, or material, that allows acoustic energy to be transferred from portion 118 of object 102 to acousto-optical sensor 132 without substantially impeding this transfer of acoustic energy. This substance may have acoustic properties that are similar to portion 118 of object 102 and may also have properties that allow a sufficient level of contact and coupling between portion 118 and acousto-optical sensor 132. The substance may provide low reflection of acoustic energy but high transfer of the acoustic energy. In some cases, the substance may be referred to as an acoustically-matched material. The substance may take the form of, for example, but not limited to, water, rubber, glue, gel, some other type of fluid, solid, or semi-solid substance, or some combination thereof.

For example, acoustic coupling element 141 may take the form of a hollow plate filled with a fluid. The fluid may be comprised of any number of gases, any number of liquids, or some combination thereof. For example, the fluid may be a liquid, such as water. The fluid may be the medium used to facilitate transmission of acoustic energy 140 to acousto-optical sensor 132. In another example, acoustic coupling element 141 may take the form of a gel, an adhesive material, a rubber material, or some other type of material.

Acousto-optical sensor 132 generates image 142 based on vibratory response 139 detected by acousto-optical sensor 132. In particular, acousto-optical sensor 132 converts amplitude of acoustic energy 140 into optical intensity to form image 142. In this illustrative example, image 142 is of portion 118 of object 102. Image 142 is visually presented at second side 136 of acousto-optical sensor 132.

When a feature of interest, such as feature 144, is present within portion 118 of object 102, image 142 may include a visual representation of the feature of interest. In this manner, image 142 may be used to determine when a feature of interest, such as feature 144, is present within portion 118 of object 102.

For example, when feature 144 is present within portion 118 of object 102, vibratory response 139 of portion 118 of object 102 includes feature response 146. Feature response 146 may be any portion of vibratory response 139 that is different, and thus distinguishable, from a rest of vibratory response 139. For example, feature 144 may respond differently to the excitation of portion 118 of object 102 as compared to a rest of portion 118. Thus, the vibratory response of feature 144, herein referred to as feature response 146, may be different from the vibratory response of the rest of portion 118. In one illustrative example, feature response 146 may be a portion of vibratory response 139 that is more nonlinear than the rest of vibratory response 139, which may be more linear.

For example, when vibration generator 108 excites object 102 such that portion 118 of object 102 resonates, a resonance pattern may be created. The resonance pattern created by portion 118 of object 102 having feature 144 may be different from the resonance pattern created when feature 144 is not present. The difference between these two resonance patterns may be feature response 146.

Consequently, image 142 produced when feature 144 is present may be different from image 142 produced when feature 144 is not present. When feature 144 is present, image 142 may include a visual representation of feature 144 that is distinguishable from the rest of portion 118 of object 102 in image 142. For example, image 142 may include indication 148 that feature 144 is present.

Indication 148, and thereby image 142, may change in response to a change in the frequency at which object 102 is excited using vibration generator 108. These changes to image 142 may be produced in substantially real-time or near real-time with respect to the changes in the frequency. In some cases, indication 148 may only be present or readily distinguishable in image 142 at certain frequencies.

In these illustrative examples, indication 148 of feature 144 may be easily and readily distinguishable such that even a non-expert may be able to identify indication 148 of feature 144 in image 142. The location of indication 148 within image 142 may correspond to a location of feature 144 within portion 118 of object 102. In this manner, a human operator, including a non-expert, may easily and quickly be able to at least determine when a feature of interest, such as feature 144, is present and locate that feature of interest in object 102.

Further, image 142 may be generated in substantially real-time such that a feature of interest may be detected and evaluated without significant delay. In particular, acousto-optical sensor 132 may be configured to detect vibratory response 139 and generate image 142 immediately or almost immediately after object 102 is excited using vibration generator 108.

The feature of interest may be detected in a number of different ways. For example, without limitation, a comparison of image 142 to a collection of images associated with specific features of interest may be made. In particular, this comparison may determine whether image 142 substantially matches or is similar to any images in the collection of images that are known to visually represent the feature of interest. The comparison may be performed by a human operator or a computer system, depending on the implementation.

Number of acousto-optical sensors 130 may include one or more acousto-optical sensors having any number of shapes and sizes. When multiple acousto-optical sensors are included, these acousto-optical sensors may be coupled to different portions of object 102 at the same time. In this manner, different portions of object 102 may be quickly and easily inspected at substantially the same time. This type of inspection may provide the ability to compare different features of interest within the different portions of object 102 relative to each other.

As described above, nondestructive inspection system 106 may include imaging system 112. Imaging system 112 may take the form of a camera, a video camera, or some other type of imaging system. Imaging system 112 may be positioned away from acousto-optical sensor 132 such that second side 136 of acousto-optical sensor 132 is within a field of view of imaging system 112.

Imaging system 112 may be used to generate number of images 150 that captures image 142 visually presented at second side 136 of acousto-optical sensor 132. In one illustrative example, number of images 150 may be sent to computer system 152 over one or more communications links. Computer system 152 may be comprised of one or more computers in communication with each other. Computer system 152 may be located entirely within inspection environment 100, entirely outside of inspection environment 100, or partially within inspection environment 100.

When computer system 152 is located outside of inspection environment 100 in a remote location, remote expert 154 may use computer system 152 to view and analyze number of images 150. Remote expert 154 may be an expert having a desired level of knowledge and skill with respect to nondestructive inspection who is not located proximal to object 102. In other words, remote expert 154 may be an expert who is located remotely with respect to object 102.

In some cases, number of images 150 may be sent to computer system 152 as number of images 150 are generated such that remote expert 154 may view number of images 150 in substantially real time. In other illustrative examples, number of images 150 may be stored on computer system 152 for later viewing and evaluation by remote expert 154, some other human operator, or a program.

The illustration of inspection environment 100 in FIG. 1 is not meant to imply physical or architectural limitations to the manner in which an illustrative embodiment may be implemented. Other components in addition to or in place of the ones illustrated may be used. Some components may be optional. Also, the blocks are presented to illustrate some functional components. One or more of these blocks may be combined, divided, or combined and divided into different blocks when implemented in an illustrative embodiment.

For example, in some cases, imaging system 112 may not be included in nondestructive inspection system 106. In some illustrative examples, number of images 150 may be sent to a number of remote servers in addition to or in place of computer system 152. In other illustrative examples, acousto-optical system 110 may take the form of a plurality of acousto-optical sensors having a grid-type arrangement or some type of other arrangement or configuration. Using multiple acousto-optical sensors may allow portions of an object having different shapes and sizes to be inspected substantially simultaneously. Further, when using multiple acousto-optical sensors, the configuration of the acousto-optical sensors relative to each other may be changed during inspection of object 102.

As one illustrative example, ten acousto-optical sensors may be used to inspect portion 118 of object 102 rather than a single acousto-optical sensor. These acousto-optical sensors may be arranged in a grid pattern or some other pattern over portion 118 of object 102. At a later time, a different portion of object 102 may need to be inspected. This portion may be smaller than portion 118 of object 102. All ten acousto-optical sensors may be unable to properly fit over this portion. Rather, only five acousto-optical sensors may be needed to cover this portion.

In this manner, using multiple smaller-sized acousto-optical sensors instead of a single larger-sized acousto-optical sensor may allow portions of different shapes and sizes to be easily inspected. In some cases, this type of implementation may reduce the overall cost of acousto-optical sensors needed.

Figure 2:
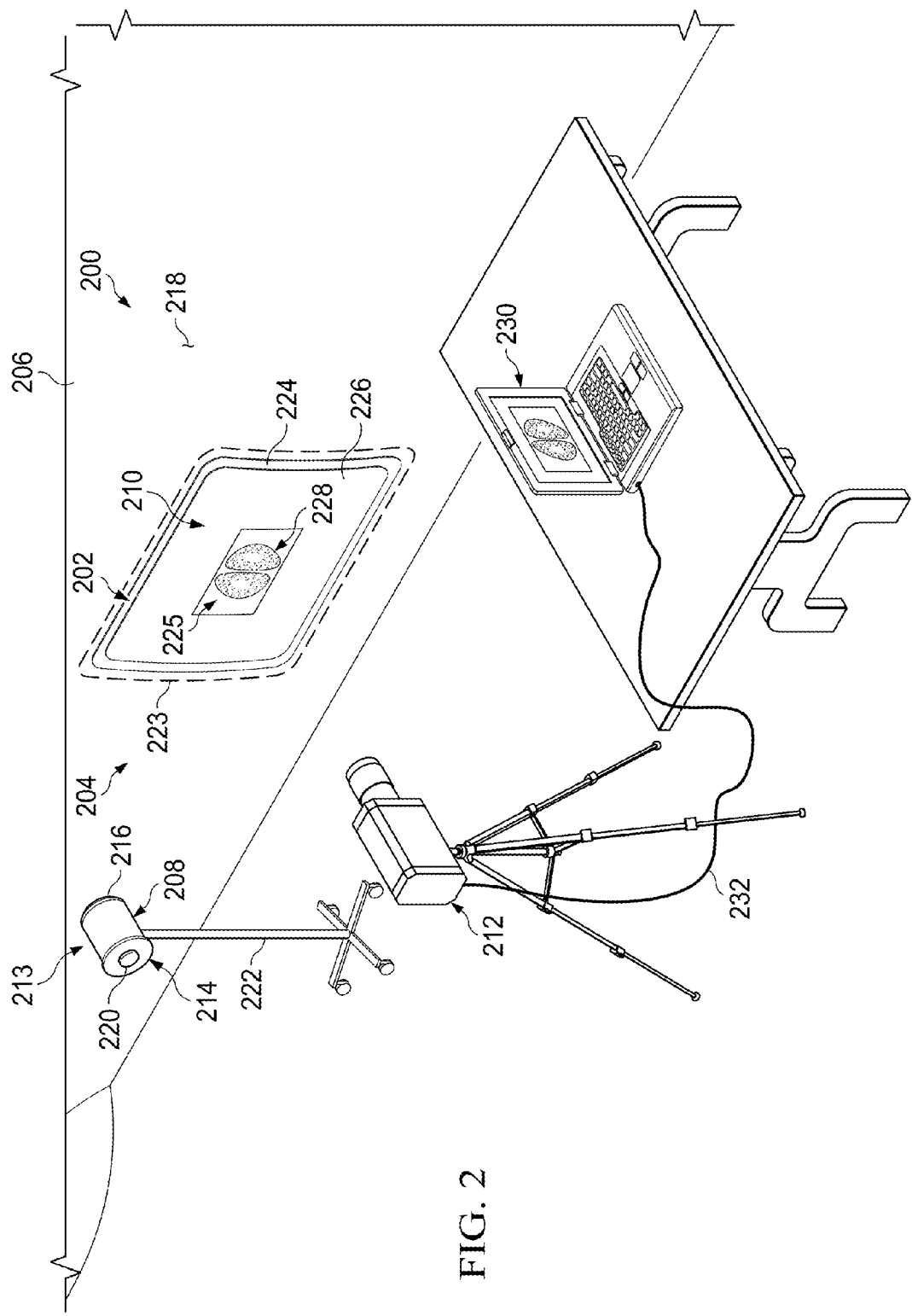
FIG. 2 is an illustration of an inspection environment in accordance with an illustrative embodiment.

With reference now to FIG. 2, an illustration of an inspection environment is depicted in accordance with an illustrative embodiment. In this illustrative example, inspection environment 200 may be an example of one implementation for inspection environment 100 in FIG. 1.

In inspection environment 200, nondestructive inspection system 202 is used to inspect aircraft structure 204. Aircraft structure 204 is an example of one implementation for aircraft structure 104 in FIG. 1. In this illustrative example, aircraft structure 204 is fuselage 206.

Nondestructive inspection system 202 is an example of one implementation for nondestructive inspection system 106 in FIG. 1. Nondestructive inspection system 202 includes vibration generator 208, acousto-optical sensor 210, and imaging system 212, which may be examples of implementations for vibration generator 108, acousto-optical sensor 132, and imaging system 112, respectively, in FIG. 1.

Vibration generator 208 mechanically excites aircraft structure 204 at location 213 on aircraft structure 204 such that at least portion 223 of aircraft structure 204 vibrates. In this illustrative example, vibration generator 208 takes the form of mechanical resonator 214. Mechanical resonator 214 has end 216 that contacts surface 218 of aircraft structure 204 to excite at least portion 223 of object aircraft structure 204. End 216 may contact surface 218 repeatedly at a frequency selected to cause a feature of interest within portion 223 to vibrate in a particular manner. In this illustrative example, the frequency may be selected to cause amplified vibration of the feature of interest. In some cases, the frequency may be selected to cause the feature of interest to resonate.

In other illustrative examples, the frequency with which end 216 contacts surface 218 may be changed to perform a frequency sweep across a range of frequencies. For example, a plurality of preselected frequencies that are selected to perform a frequency sweep of portion 223 of aircraft structure 204 may be used to excite portion 223 of aircraft structure 204.

In another example, the frequency may be swept through a continuous range of frequencies, such as from about 10 kilohertz to about 200 kilohertz. In yet another example, the range of frequencies may be a discontinuous range that includes the frequencies at some selected interval from about 10 kilohertz to about 200 kilohertz. For example, the frequency at every 1 kilohertz, 5 kilohertz, 10 kilohertz, 20 kilohertz, 50 kilohertz, or some other selected interval within a particular range may be included. The range of frequencies may be selected such that excitation of portion 223 of aircraft structure 204 will produce amplified vibration or in particular, resonance, of the feature of interest.

The particular frequency or range of frequencies selected for use in exciting portion 223 of aircraft structure 204 with vibration generator 208 may be based on, for example, test results performed using a reference object or standard for aircraft structure 204. As one illustrative example, the standard may be excited at different frequencies until the particular frequency at which the standard resonates is identified. This particular frequency or some range of frequencies around this particular frequency may then be used to inspect aircraft structure 204.

Frequency control 220 may be used to control the frequency at which vibration generator 208 excites aircraft structure 204 at location 213 of aircraft structure 204. In this illustrative example, frequency control 220 may be controlled by a human operator, a computer, a processor unit in vibration generator 208, a microprocessor, or some other type of controller.

As depicted, vibration generator 208 is portably mounted on wheeled stand 222. Wheeled stand 222 may be used to move and position vibration generator 208 relative to aircraft structure 204. In this illustrative example, wheeled stand 222 may also be used to adjust a height of vibration generator 208 relative to aircraft structure 204.

In other illustrative examples, other means of moving vibration generator 208 may be used. For example, some other type of device, including, but not limited to, a robotic device, a positioning system, a movement system, an automated movement system, or some other type of device may be used to move vibration generator 208 relative to aircraft structure 204.

Acousto-optical sensor 210 is coupled to surface 218 of aircraft structure 204. In particular, acousto-optical sensor 210 is coupled to surface 218 of portion 223 of aircraft structure 204 using vacuum seal 224. Vacuum seal 224 is an example of one implementation for coupling element 138 in FIG. 1. Vacuum seal 224 retains a first side (not shown in this view) of acousto-optical sensor 210 in physical contact against surface 218. This type of coupling of acousto-optical sensor 210 to surface 218 of aircraft structure 204 is simple, may be performed quickly, and may not require an expert to be performed.

In this illustrative example, acousto-optical sensor 210 visually presents image 225 of portion 223 on second side 226 of acousto-optical sensor 210. Image 225 may be generated by acousto-optical sensor 210 based on the vibratory response of aircraft structure 204 to excitation by vibration generator 208 as detected by acousto-optical sensor 210.

Image 225 includes indication 228 of a feature of interest. Indication 228 is a visual representation of a feature of interest within portion 223 of aircraft structure 204. Indication 228 may be, for example, without limitation, one or more colors that indicate an amplified vibratory response of the feature of interest as compared to the vibratory response of the rest of portion 223 of aircraft structure 204.

The feature of interest may be hidden under surface 218 of aircraft structure 204 but detectable based on the vibratory response of aircraft structure 204 to excitation by vibration generator 208. Indication 228 may reflect that portion 223 of aircraft structure 204 has a different resonance pattern than the resonance pattern that portion 223 would have if the feature of interest were not present. This determination may be made by reference to standard vibrations for aircraft structure 204 being evaluated. In this manner, indication 228 provides a simple way to determine in substantially real-time whether or not the feature of interest is present.

Figure 7:
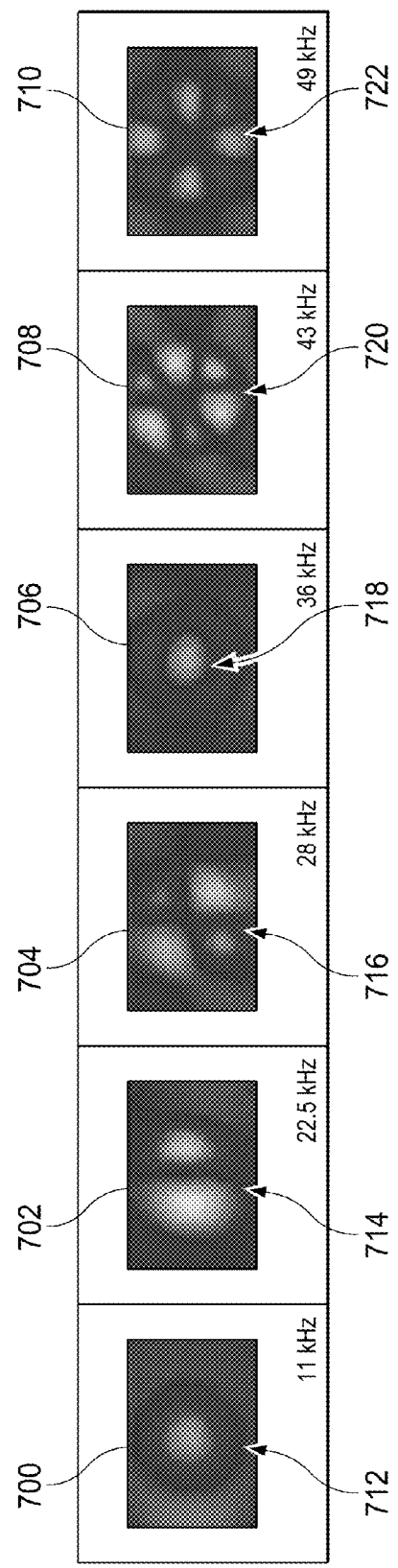
FIG. 7 is an illustration of images generated using an acousto-optical sensor in accordance with an illustrative embodiment.

Changing the frequency at which vibration generator 208 excites aircraft structure 204 may change image 225. Examples of different images that may be generated for the feature of interest in portion 223 of aircraft structure 204 at different excitation frequencies is depicted in FIG. 7, described below.

In this illustrative example, imaging system 212 is used to generate images that capture second side 226 of acousto-optical sensor 210. Imaging system 212 is positioned away from acousto-optical sensor 210 such that second side 226 of acousto-optical sensor 210 is within the field of view of imaging system 212. Imaging system 212 may be a video camera configured to generate video comprising a sequence of images. In another illustrative example, imaging system 212 may be a camera configured to generate still images.

The images generated by imaging system 212 are sent to computer 230 over wired communications link 232 in this illustrative example. In other examples, the images may be sent over a wireless communications link, an optical communications link, or some other type of communications link to computer 230 or some other computer system located remotely. For example, the images generated by imaging system 212 may be sent wirelessly to a remote computer system such that an expert located remotely may be able to view and analyze the images in substantially real-time or at a later time.

Figure 3:
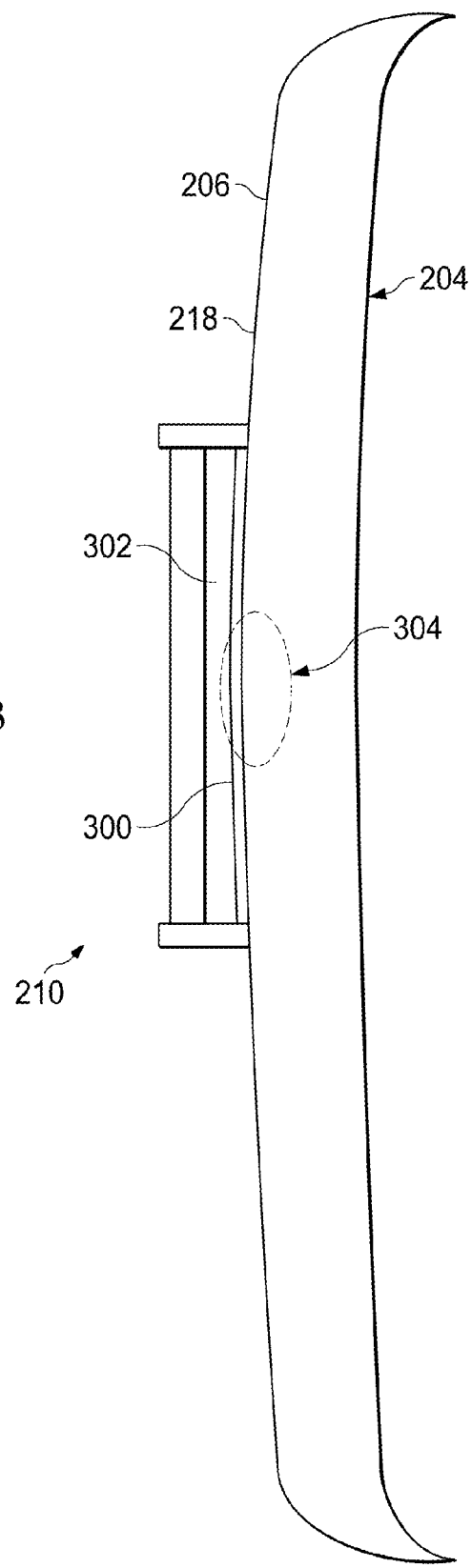
FIG. 3 is an illustration of a cross-sectional side view of an acousto-optical sensor and an aircraft structure in accordance with an illustrative embodiment.

With reference now to FIG. 3, an illustration of a cross-sectional side view of acousto-optical sensor 210 and aircraft structure 204 from FIG. 2 is depicted in accordance with an illustrative embodiment. In this illustrative example, first side 300 of acousto-optical sensor 210 is shown.

Acoustic coupling element 302 is associated with acousto-optical sensor 210 at first side 300 of acousto-optical sensor 210. Acoustic coupling element 302 facilitates the transmission of acoustic energy generated by portion 223 of aircraft structure 204 in response to excitation by vibration generator 208 in FIG. 2 to acousto-optical sensor 210. Acoustic coupling element 302 ensures that the vibratory response of aircraft structure 204 is detected by acousto-optical sensor 210 with a desired level of accuracy.

Feature 304 within portion 223 of aircraft structure 204 is seen in FIG. 3. Feature 304 is an example of a feature of interest. In some cases, feature 304 may be an undesired feature. Indication 228 in image 225 in FIG. 2 is a visual representation of feature 304.

Figure 4:
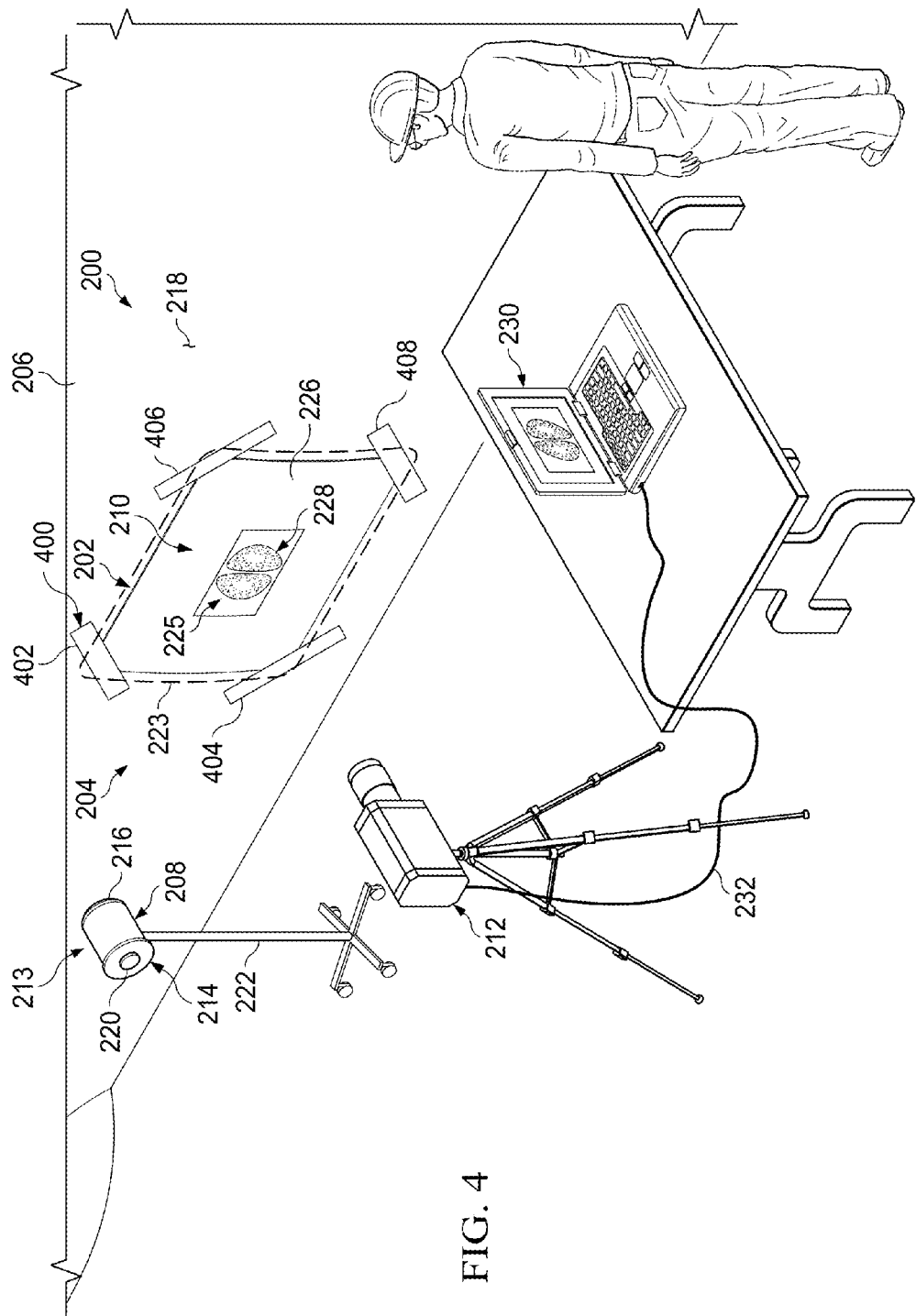
FIG. 4 is an illustration of a different type of coupling element used to retain an acousto-optical sensor against a surface of an aircraft structure in accordance with an illustrative embodiment.

With reference now to FIG. 4, an illustration of a different type of coupling element used to retain acousto-optical sensor 210 against surface 218 of aircraft structure 204 from FIG. 2 is depicted in accordance with an illustrative embodiment. In this illustrative example, adhesive 400 is used to couple acousto-optical sensor 210 to surface 218 of portion 223 of aircraft structure 204.

Adhesive 400 is an example of one implementation for coupling element 138 in FIG. 1. Adhesive 400 is implemented using temporary adhesive strip 402, temporary adhesive strip 404, temporary adhesive strip 406, and temporary adhesive strip 408. This type of coupling of acousto-optical sensor 210 to surface 218 of aircraft structure 204 is simple, may be performed quickly, and does not require an expert to be performed.

Figure 5:
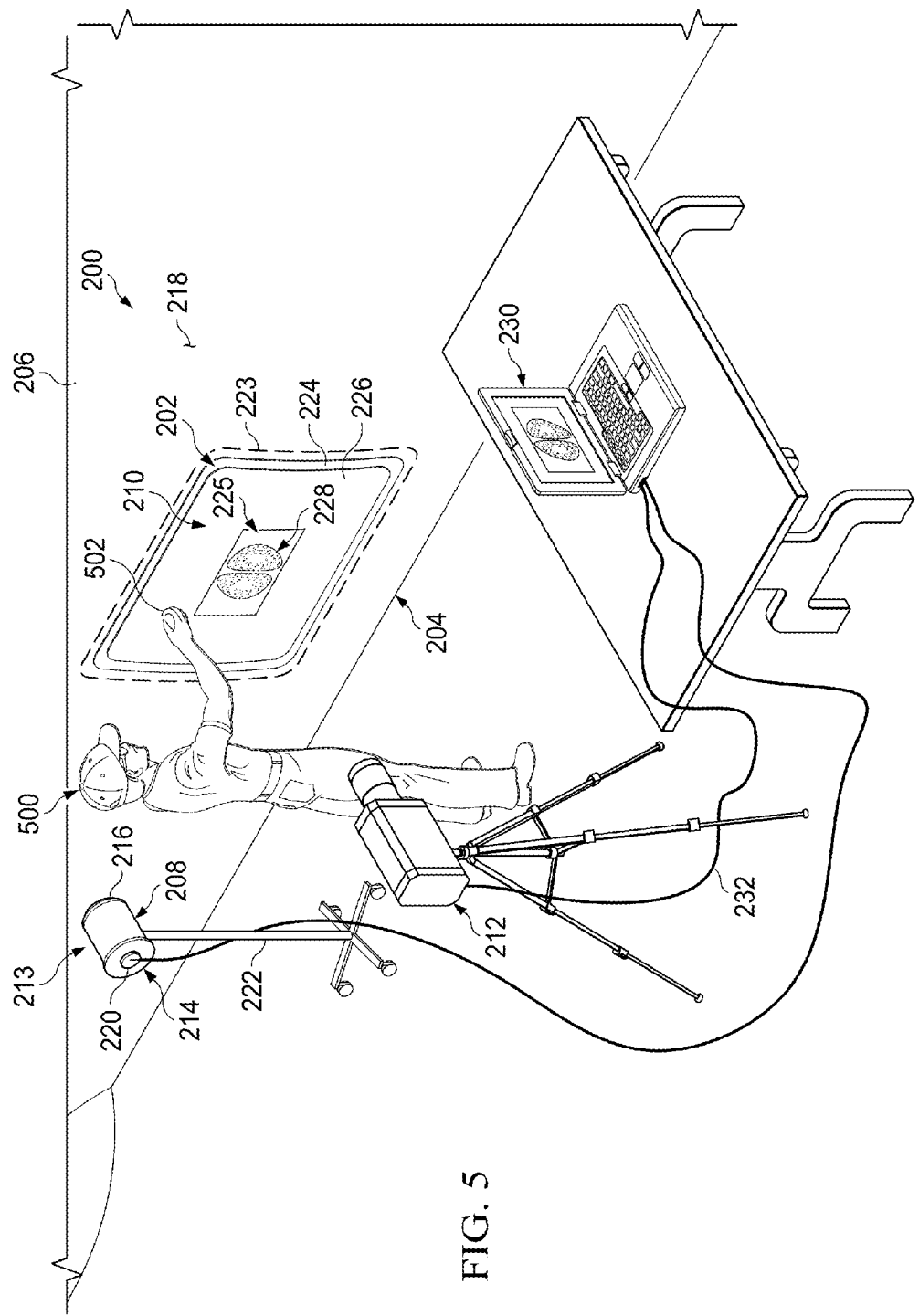
FIG. 5 is an illustration of a different type of coupling element used to retain an acousto-optical sensor against a surface of an aircraft structure in accordance with an illustrative embodiment.

With reference now to FIG. 5, an illustration of a different type of coupling element used to retain acousto-optical sensor 210 against surface 218 of aircraft structure 204 from FIG. 2 is depicted in accordance with an illustrative embodiment. In this illustrative example, mechanical pressure is used to couple acousto-optical sensor 210 to surface 218 of portion 223 of aircraft structure 204.

In particular, human operator 500 may use hand 502 to apply mechanical pressure to acousto-optical sensor 210 to hold acousto-optical sensor 210 in a fixed position relative to aircraft structure 204. This type of coupling of acousto-optical sensor 210 to surface 218 of aircraft structure 204 is simple, may be performed quickly, and does not require an expert to be performed.

Figure 6:
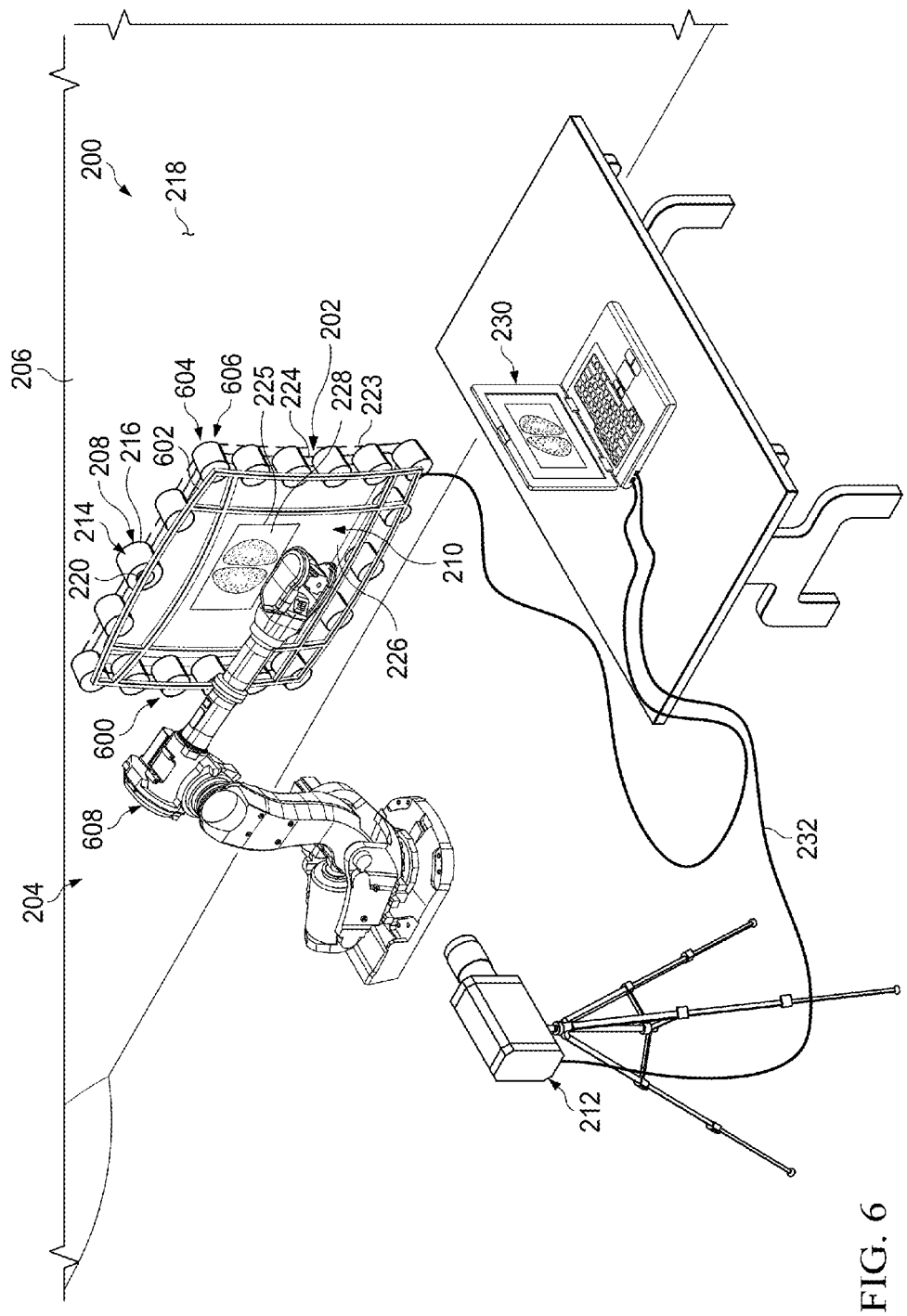
FIG. 6 is an illustration of an integrated ultrasonic imaging system in accordance with an illustrative embodiment.

With reference now to FIG. 6, an illustration of an integrated ultrasonic imaging system is depicted in accordance with an illustrative embodiment. In this illustrative example, vibration generator 208 and acousto-optical sensor 210 from FIGS. 2-5 have been integrated to form integrated ultrasonic imaging system 600.

In particular, vibration generator 208 and acousto-optical sensor 210 have been associated with each other using retaining member 602. As depicted, vibration generator 208 is associated with retaining member 602 by being mounted to retaining member 602. Further, acousto-optical sensor 210 is also associated with retaining member 602. In particular, an outer edge of acousto-optical sensor 210 may be associated with retaining member 602. Retaining member 602 holds vibration generator 208 in place relative to acousto-optical sensor 210.

Integrated ultrasonic imaging system 600 also includes adhesion system 604. Adhesion system 604 may be a vacuum adhesion system comprised of plurality of adhesion members 606. Adhesion system 604 may be an example of one implementation for coupling element 138 in FIG. 1.

In one illustrative example, each of plurality of adhesion members 606 may be implemented as a structure having a seal associated with the structure and in communication with a channel within the structure. The seal may be configured to adhere to surface 218 of aircraft structure 204 when air is drawn into the channel of the structure through the seal. In some cases, the seal may be configured to rotate relative to the structure to at least partially conform to a shape of surface 218. A gap, or "air cushion," may be created between the seal and surface 218. The gap may function as an air bearing such that the seal "floats" over surface 218.

In this manner, plurality of adhesion members 606 may be used to form non-contact vacuum adhesion to surface 218 such that plurality of adhesion members 606 may "float" above surface 218. This non-contact vacuum adhesion may hold vibration generator 208 and acousto-optical sensor 210 in place relative to each other and to surface 218 of aircraft structure 204. Although plurality of adhesion members 606 may float over surface 218, the vacuum adhesion of acousto-optical sensor 210 to surface 218 resulting from the air being drawn through plurality of adhesion members 606 may be sufficiently strong to hold acousto-optical sensor 210 in place.

However, the vacuum adhesion may not be so strong as to prevent plurality of adhesion members 606 from being pulled away from surface 218 with sufficient force or from plurality of adhesion members 606 being moved along surface 218 with sufficient force. For example, plurality of adhesion members 606 may be used to adhere acousto-optical sensor 210 to one location on surface 218 for inspection. After inspection of this location, plurality of adhesion members 606 may be pulled away from surface 218. Then, plurality of adhesion members 606 may be moved to a new location on surface 218 and used to adhere acousto-optical sensor 210 to surface 218 at this new location for inspection of this new location. This process may be repeated any number of times such that any number of locations on surface 218 may be inspected.

As depicted, robotic device 608 may be associated with integrated ultrasonic imaging system 600 by being associated with retaining member 602. Robotic device 608 may be used to move and position retaining member 602, and thus the entirety of integrated ultrasonic imaging system 600, relative to surface 218 of aircraft structure 204. In some cases, the movement of retaining member 602 and integrated ultrasonic imaging system 600 by robotic device 608 may be automated such that integrated ultrasonic imaging system 600 is moved to a plurality of predefined locations on aircraft structure 204 or along some predefined pathway along surface 218.

In other illustrative examples, integrated ultrasonic imaging system 600 may be moved relative to aircraft structure 204 manually by a human operator. For example, the human operator may use handles (not shown in this view) on retaining member 602 to move integrated ultrasonic imaging system 600.

With reference now to FIG. 7, an illustration of images generated using an acousto-optical sensor is depicted in accordance with an illustrative embodiment. In this illustrative example, image 700, image 702, image 704, image 706, image 708, and image 710 may be generated by acousto-optical sensor 210 from FIG. 2. These images may all be images of portion 223 of aircraft structure 204 in FIG. 2.

As depicted, image 700, image 702, image 704, image 706, image 708, and image 710 include indication 712, indication 714, indication 716, indication 718, indication 720, and indication 722, respectively. Each of these indications is a visual representation of feature 304 shown in FIG. 3.

Each of image 700, image 702, image 704, image 706, image 708, and image 710 is generated based on the vibratory response of portion 223 of aircraft structure 204 to excitation at a different frequency. In this illustrative example, image 700, image 702, image 704, image 706, image 708, and image 710 may correspond to excitation frequencies at about 11 kilohertz, about 22.500 kilohertz, about 28 kilohertz, about 36 kilohertz, about 43 kilohertz, and about 49 kilohertz, respectively.

The illustrations of inspection environment 200 in FIGS. 2 and 4-6, acousto-optical sensor 210 in FIG. 3, and the images shown in FIG. 7 are not meant to imply physical or architectural limitations to the manner in which an illustrative embodiment may be implemented. Other components in addition to or in place of the ones illustrated may be used. Some components may be optional.

The different components shown in FIGS. 2-6 may be illustrative examples of how components shown in block form in FIG. 1 can be implemented as physical structures. Additionally, some of the components in FIGS. 2-6 may be combined with components in FIG. 1, used with components in FIG. 1, or a combination of the two. Further, the images shown in FIG. 7 may only be examples of the types of images and types of indications that may be generated for a feature of interest at different frequencies.

For example, in some cases, vibration generator 208 and acousto-optical sensor 210 may be associated with each other in some manner other than retaining member 602 shown in FIG. 6. In some illustrative examples, a human operator may be used to move and position vibration generator 208 relative to surface 218 of aircraft structure 204. For example, a human operator may hold vibration generator 208 in one hand relative to surface 218 of aircraft structure 204, while holding acousto-optical sensor 210 against surface 218 of aircraft structure 204 in the other hand.

Figure 8:
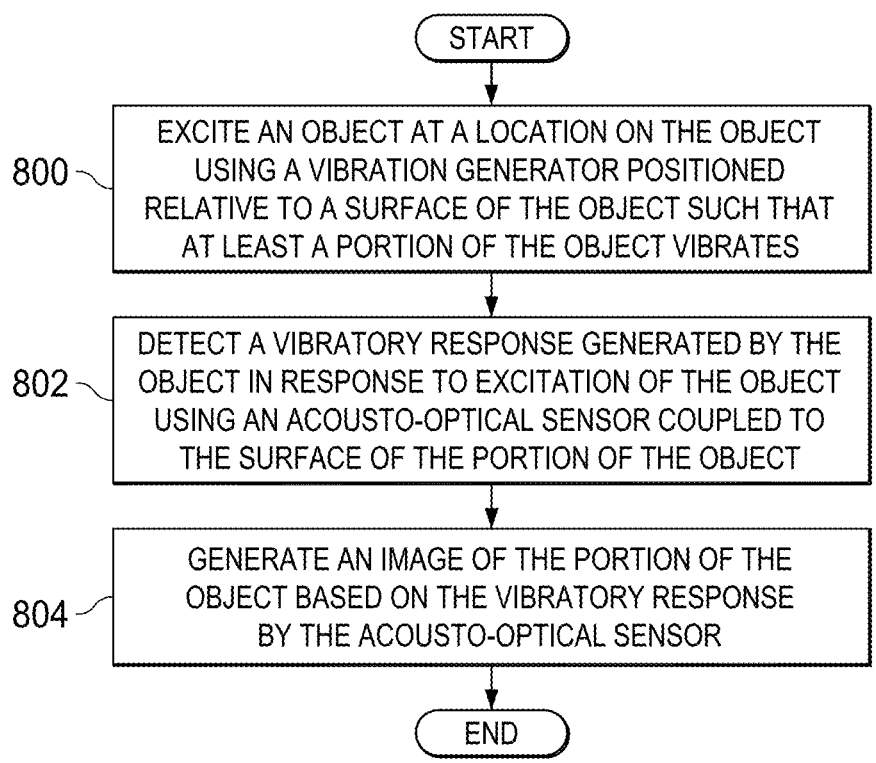
FIG. 8 is an illustration of a process for inspecting an object in the form of a flowchart in accordance with an illustrative embodiment.

With reference now to FIG. 8, an illustration of a process for inspecting an object is depicted in the form of a flowchart in accordance with an illustrative embodiment. The process illustrated in FIG. 8 may be implemented using nondestructive inspection system 106 in FIG. 1.

The process begins by exciting an object at a location on the object using a vibration generator positioned relative to a surface of the object such that at least a portion of the object vibrates (operation 800). In operation 800, the portion of the object may be excited at a particular frequency selected to cause a feature of interest to produce a feature response. In other illustrative examples, the object may be excited over a range of frequencies to perform a frequency sweep to inspect for one or more features of interest.

A vibratory response generated by the object in response to excitation of the object is detected using an acousto-optical sensor coupled to the surface of the portion of the object (operation 802). An image of the portion of the object is generated based on the vibratory response by the acousto-optical sensor (operation 804), with the process terminating thereafter.

When a feature of interest is present within the portion of the object, the image generated in operation 804 may include a visual representation of the feature. In particular, the image may include an indication that the feature is present. This indication may be easily distinguishable. Thus, a human operator may be able to quickly determine whether a feature of interest is present based on the image.

The overall process described in FIG. 8 may be repeated any number of times such that any number of portions of the object may be inspected. For example, the vibration generator may be repositioned relative to the object and coupled to another portion of the object. The repositioning of the vibration generator may include translating the vibration generator, rotating the vibration generator, or both. In this manner, different portions of the object may be quickly and easily inspected.

Figure 9:
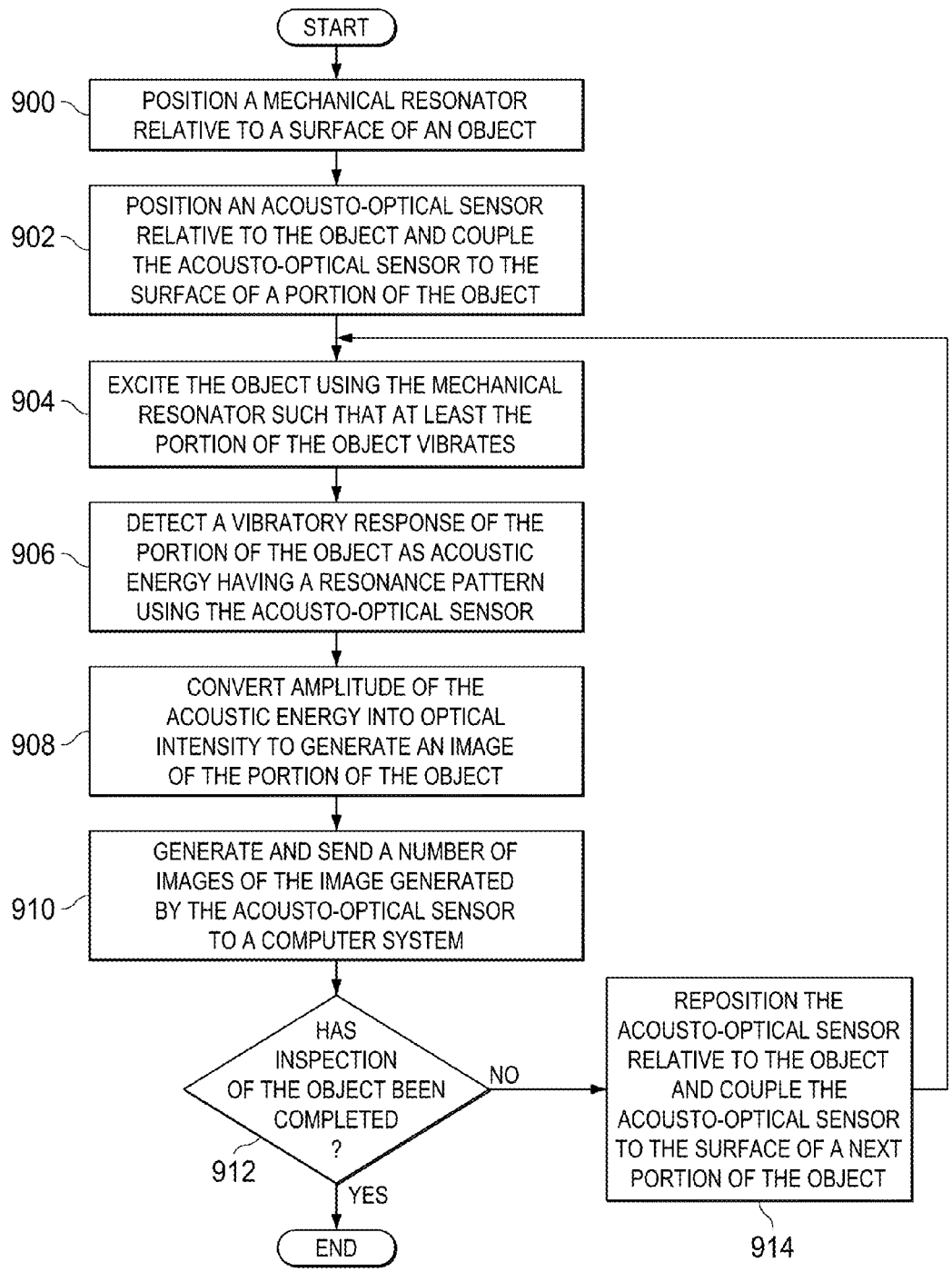
FIG. 9 is an illustration of a process for inspecting an object in the form of a flowchart in accordance with an illustrative embodiment.

With reference now to FIG. 9, an illustration of a process for inspecting an object is depicted in the form of a flowchart in accordance with an illustrative embodiment. The process illustrated in FIG. 9 may be implemented using nondestructive inspection system 106 in FIG. 1.

The process begins by positioning a mechanical resonator relative to a surface of an object (operation 900). In some cases, in operation 900, the mechanical resonator may be coupled to the surface of the object.

Next, an acousto-optical sensor is positioned relative to the object and coupled to the surface of a portion of the object (operation 902). This portion may be an area, a section, or a part of the object designated for inspection. The object is then excited using the mechanical resonator such that at least the portion of the object vibrates (operation 904). Depending on the frequency or frequencies at which the portion of the object is excited, a feature of interest, when present within the portion of the object, may resonate.

A vibratory response of the portion of the object is detected as acoustic energy having a resonance pattern using the acousto-optical sensor (operation 906). When a feature of interest is present within the portion of the object and resonates in response to excitation of the portion of the object, the vibratory response detected in operation 906 may include a feature response.

Amplitude of the acoustic energy is converted into optical intensity to generate an image of the portion of the object (operation 908). When the vibratory response detected in operation 906 includes the feature response, the image generated in operation 908 includes an indication that visually represents the feature of interest.

A number of images of the image generated by the acousto-optical sensor are generated and sent to a computer system (operation 910). In one illustrative example, operation 910 may be performed using an imaging system positioned relative to the acousto-optical sensor such that the acousto-optical sensor is within the field of view of the imaging system.

Thereafter, a determination is made as to whether inspection of the object has been completed (operation 912). If the inspection of the object has been completed, the process terminates. Otherwise, the process repositions the acousto-optical sensor relative to the object and couples the acousto-optical sensor to the surface of a next portion of the object (operation 914), with the process then returning to operation 904 as described above.

The flowcharts and block diagrams in the different depicted embodiments illustrate the architecture, functionality, and operation of some possible implementations of apparatuses and methods in an illustrative embodiment. In this regard, each block in the flowcharts or block diagrams may represent a module, a segment, a function, a portion of an operation or step, some combination thereof.

In some alternative implementations of an illustrative embodiment, the function or functions noted in the blocks may occur out of the order noted in the figures. For example, in some cases, two blocks shown in succession may be executed substantially concurrently, or the blocks may sometimes be performed in the reverse order, depending upon the functionality involved. Also, other blocks may be added in addition to the illustrated blocks in a flowchart or block diagram.

Figure 10:
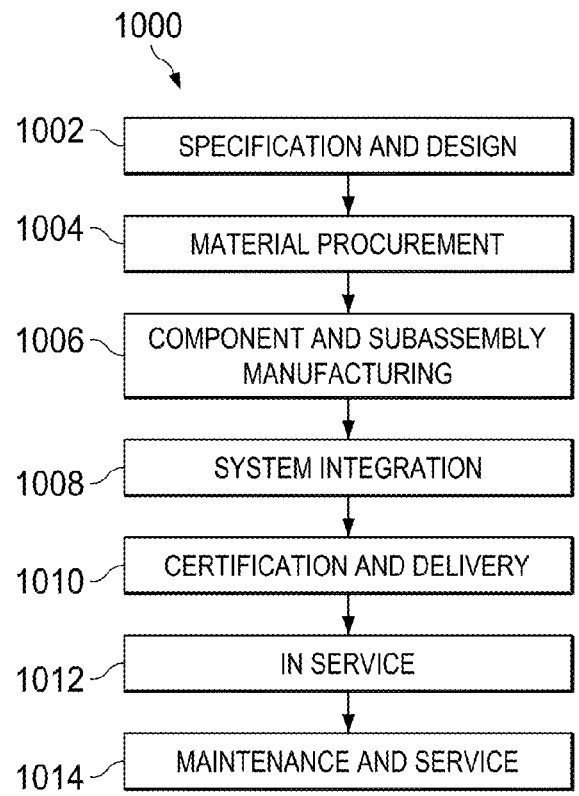
FIG. 10 is an illustration of an aircraft manufacturing and service method in the form of a block diagram in accordance with an illustrative embodiment.
Figure 11:
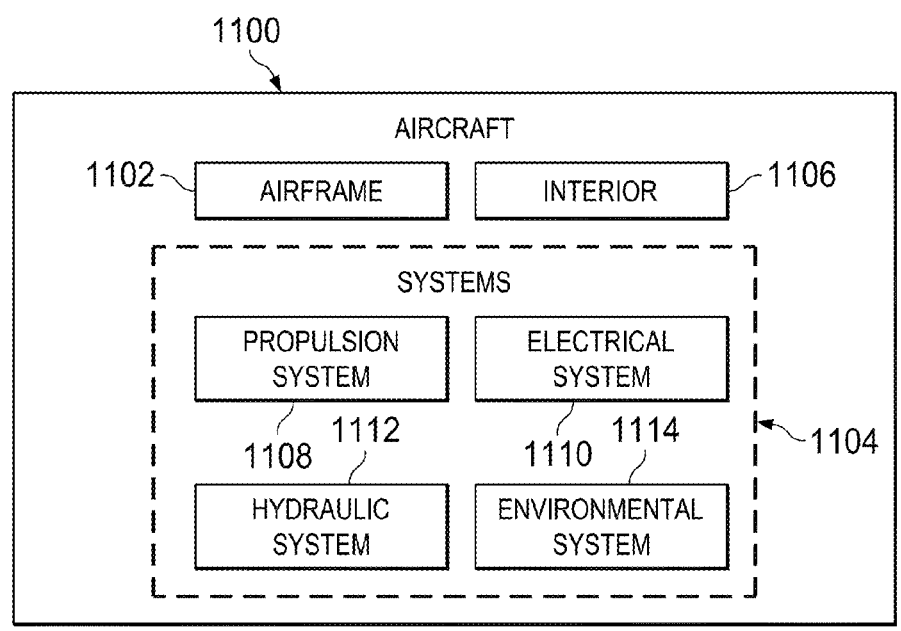
FIG. 11 is an illustration of an aircraft in the form of a block diagram in which an illustrative embodiment may be implemented.

The illustrative embodiments of the disclosure may be described in the context of aircraft manufacturing and service method 1000 as shown in FIG. 10 and aircraft 1100 as shown in FIG. 11. Turning first to FIG. 10, an illustration of an aircraft manufacturing and service method is depicted in the form of a block diagram in accordance with an illustrative embodiment. During pre-production, aircraft manufacturing and service method 1000 may include specification and design 1002 of aircraft 1100 in FIG. 11 and material procurement 1004.

During production, component and subassembly manufacturing 1006 and system integration 1008 of aircraft 1100 in FIG. 11 takes place. Thereafter, aircraft 1100 in FIG. 11 may go through certification and delivery 1010 in order to be placed in service 1012. While in service 1012 by a customer, aircraft 1100 in FIG. 11 is scheduled for routine maintenance and service 1014, which may include modification, reconfiguration, refurbishment, and other maintenance or service.

Each of the processes of aircraft manufacturing and service method 1000 may be performed or carried out by at least one of a system integrator, a third party, or an operator. In these examples, the operator may be a customer. For the purposes of this description, a system integrator may include, without limitation, any number of aircraft manufacturers and major-system subcontractors; a third party may include, without limitation, any number of vendors, subcontractors, and suppliers; and an operator may be an airline, a leasing company, a military entity, a service organization, and so on.

With reference now to FIG. 11, an illustration of an aircraft is depicted in the form of a block diagram in which an illustrative embodiment may be implemented. In this example, aircraft 1100 is produced by aircraft manufacturing and service method 1000 in FIG. 10 and may include airframe 1102 with plurality of systems 1104 and interior 1106. Examples of systems 1104 include one or more of propulsion system 1108, electrical system 1110, hydraulic system 1112, and environmental system 1114. Any number of other systems may be included. Although an aerospace example is shown, different illustrative embodiments may be applied to other industries, such as the automotive industry.

The apparatuses and methods embodied herein may be employed during at least one of the stages of aircraft manufacturing and service method 1000 in FIG. 10. In particular, nondestructive inspection system 106 from FIG. 1 may be used to inspect a structure of aircraft 1100 during any one of the stages of aircraft manufacturing and service method 1000. For example, without limitation, nondestructive inspection system 106 from FIG. 1 may be used to inspect one or more aircraft structures during at least one of component and subassembly manufacturing 1006, system integration 1008, certification and delivery 1010, in service 1012, routine maintenance and service 1014, or some other stage of aircraft manufacturing and service method 1000. Still further, nondestructive inspection system 106 from FIG. 1 may be used to inspect airframe 1102, interior 1106, or any one of plurality of systems 1104 of aircraft 1100.

In one illustrative example, components or subassemblies produced in component and subassembly manufacturing 1006 in FIG. 10 may be fabricated or manufactured in a manner similar to components or subassemblies produced while aircraft 1100 is in service 1012 in FIG. 10. As yet another example, one or more apparatus embodiments, method embodiments, or a combination thereof may be utilized during production stages, such as component and subassembly manufacturing 1006 and system integration 1008 in FIG. 10. One or more apparatus embodiments, method embodiments, or a combination thereof may be utilized while aircraft 1100 is in service 1012, during maintenance and service 1014 in FIG. 10, or both. The use of a number of the different illustrative embodiments may substantially expedite the assembly of and reduce the cost of aircraft 1100.

Thus, the illustrative embodiments provide a method and apparatus for quickly and easily inspecting objects. The inspection method provided using nondestructive inspection system 106 in FIG. 1 may allow inspections to be performed without requiring an expert in nondestructive inspection to operate the various components of nondestructive inspection system 106. A non-expert may be able to easily operate acousto-optical sensor 132 in FIG. 1. Further, a non-expert may be able to easily and quickly determine whether a feature of interest is present in an object, such as object 102 in FIG. 1, just by looking at image 142 generated by acousto-optical sensor 132.

The non-expert may be able to mark the location on object 102 at which the feature of interest is detected without needing to understand how image 142 is generated or how to analyze image 142. Further, imaging system 112 in FIG. 1 may be used to send "still" images or video capturing image 142 generated by acousto-optical sensor 132 to an expert located remotely for analysis in substantially real-time or at a later time.

As one illustrative example, the expert may compare the "still images" or video capturing image 142 to a database of reference images in which each reference image includes a visual representation of a specific, known feature of interest. A substantial match between image 142 and one of these reference images may be a detection of the specific, known feature of interest visually represented in the reference image. Thus, nondestructive inspection system 106 may be well-suited for remote nondestructive inspection methodologies.

The description of the different illustrative embodiments has been presented for purposes of illustration and description, and is not intended to be exhaustive or limited to the embodiments in the form disclosed. Many modifications and variations will be apparent to those of ordinary skill in the art. Further, different illustrative embodiments may provide different features as compared to other desirable embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. An apparatus comprising:
a vibration generator positioned relative to a surface of an object, wherein the vibration generator excites the object at a location on the object such that at least a portion of the object vibrates; and
an acousto-optical sensor coupled to the surface of the portion of the object between the vibration generator and the surface, and uncoupled to the vibration generator, wherein the acousto-optical sensor is configured to detect a vibratory response generated by the portion of the object in response to excitation by the vibration generator of the portion of the object, and wherein the acousto-optical sensor is further configured to generate, on a surface of the acousto-optical sensor, an image of the portion of the object based on the vibratory response.

2. The apparatus of claim 1, wherein the vibratory response includes a feature response that is produced when a feature is present within the portion of the object and wherein the image of the portion of the object generated based on the feature response includes an indication that visually represents the feature.

3. The apparatus of claim 1, wherein the vibration generator is a mechanical resonator configured to cause a feature that is present within the portion of the object to resonate when a frequency at which the portion of the object is excited is substantially equal to a natural frequency of the feature within selected tolerances.

4. The apparatus of claim 3, wherein the mechanical resonator is configured to excite the portion of the object at ultrasonic frequencies between about 1 kilohertz and about 500 kilohertz and wherein the mechanical resonator is selected from one of a chirped solenoid, a mechanical impedance probe, an acoustic horn, and a speaker system.

5. The apparatus of claim 1, wherein the acousto-optical sensor is configured to convert an amplitude of acoustic energy received as the vibratory response into optical intensity to generate the image.

6. The apparatus of claim 1 further comprising:
a coupling element is configured to couple the acousto-optical sensor to the surface of the portion of the object to retain the acousto-optical sensor in a fixed position relative to the object.

7. The apparatus of claim 6, wherein the coupling element includes at least one element selected from a group consisting of a vacuum seal, an adhesive, an adhesion system, and mechanical pressure applied to the acousto-optical sensor.

8. The apparatus of claim 1, wherein the acousto-optical sensor comprises:
a first side that faces the surface of the portion of the object; and
a second side, wherein the image is visually presented directly on the second side of the acousto-optical sensor, wherein the second side is opposite the first side.

9. The apparatus of claim 8 further comprising:
an acoustic coupling element associated with the first side of the acousto-optical sensor, wherein the acoustic coupling element is configured to facilitate transmission of acoustic energy from the portion of the object to the acousto-optical sensor.

10. The apparatus of claim 9 further comprising:
an imaging system positioned away from the acousto-optical sensor, wherein the imaging system is configured to generate a number of images of the second side of the acousto-optical sensor such that the number of images captures the image visually presented by the acousto-optical sensor.

11. The apparatus of claim 9, wherein the image visually presented by the acousto-optical sensor changes in response to a change in a frequency at which the portion of the object is excited by the vibration generator.

12. A method for inspecting an object, the method comprising:

exciting the object at a location on the object using a vibration generator positioned away from a surface of the object such that at least a portion of the object vibrates;

detecting a vibratory response generated by the portion of the object in response to excitation of the object using an acousto-optical sensor coupled to the surface of the portion of the object and uncoupled from the vibration generator; and generating, by the acousto-optical sensor, an image of the portion of the object based on the vibratory response, wherein the image is generated on a surface of the acousto-optical sensor.

13. The method of claim 12, wherein detecting the vibratory response comprises:

detecting a feature response that is produced when a feature is present within the portion of the object, wherein the image generated based on the feature response when the feature is present includes an indication that visually represents the feature.

14. The method of claim 13, wherein exciting the object at the location on the object using the vibration generator comprises:

exciting the object at the location on the object at a plurality of preselected frequencies selected to perform a frequency sweep of the portion of the object to determine whether a feature of interest is present within the portion of the object.

15. The method of claim 12, wherein exciting the object at the location on the object using the vibration generator comprises:

exciting the object at the location on the object using a mechanical resonator such that at least the portion of the object vibrates, wherein a feature within the portion of the object resonates when a frequency at which the portion of the object is excited is substantially equal to a natural frequency of the feature within selected tolerances.

16. The method of claim 15, wherein exciting the object at the location on the object using the mechanical resonator comprises:

exciting the object at the location on the object at ultrasonic frequencies between about 1 kilohertz and about 500 kilohertz using the mechanical resonator such that at least the portion of the object vibrates.

17. The method of claim 12, wherein generating the image of the portion of the object comprises:

converting, by the acousto-optical sensor, an amplitude of acoustic energy received as the vibratory response into an optical intensity to generate the image.

18. The method of claim 12 further comprising:

coupling a first side of the acousto-optical sensor to the surface of the portion of the object using a coupling element to retain the acousto-optical sensor in a fixed position relative to the portion of the object; and visually presenting, by the acousto-optical sensor, the image on a second side of the acousto-optical sensor, wherein the second side is opposite the first side.

19. The method of claim 18 further comprising:

positioning an imaging system away from the acousto-optical sensor such that the second side of the acousto-optical sensor is within a field of view of the imaging system.

* * * * *